United States Patent
Bloom

(10) Patent No.: US 10,813,686 B2
(45) Date of Patent: Oct. 27, 2020

(54) ELECTROSURGICAL CUTTING INSTRUMENT

(71) Applicant: Medtronic Advanced Energy LLC, Minneapolis, MN (US)

(72) Inventor: Eliot F. Bloom, Hopkinton, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 517 days.

(21) Appl. No.: 14/632,460

(22) Filed: Feb. 26, 2015

(65) Prior Publication Data
US 2015/0265337 A1 Sep. 24, 2015

Related U.S. Application Data

(60) Provisional application No. 61/944,863, filed on Feb. 26, 2014.

(51) Int. Cl.
*A61B 18/14* (2006.01)
*A61B 18/00* (2006.01)

(52) U.S. Cl.
CPC ........ *A61B 18/1485* (2013.01); *A61B 18/148* (2013.01); *A61B 2018/0063* (2013.01);
(Continued)

(58) Field of Classification Search
CPC ............ A61B 2218/002; A61B 18/148; A61B 18/1485; A61B 2218/007;
(Continued)

(56) References Cited

U.S. PATENT DOCUMENTS

| 2,888,928 A | 6/1959 | Seiger |
| 3,682,130 A | 8/1972 | Jeffers |

(Continued)

FOREIGN PATENT DOCUMENTS

| WO | WO/98/34550 | 8/1998 |
| WO | WO/03/079911 | 10/2003 |

OTHER PUBLICATIONS

Lee et al, Comparative Study on the Long-Term Effectiveness Between Coblation-and Microdebrider-Assisted partial Turbinoplasty, Laryngoscope 116:May 2006 pp. 729-734.
(Continued)

*Primary Examiner* — Jaymi E Della
*Assistant Examiner* — Sean W Collins
(74) *Attorney, Agent, or Firm* — Dicke, Billig & Czaja, PLLC

(57) ABSTRACT

An electrosurgical device having a tubular outer shaft and an inner shaft is disclosed. The tubular outer shaft includes an axis and a distal end region. The distal end region includes a distal-most tip and a cutting edge defining a window in the outer shaft proximal along the axis to the distal-most tip. The inner shaft inner shaft coaxially maintained within the outer shaft such that the inner shaft is movable about the axis with respect to the outer shaft and wherein a portion of the inner shaft is exposed in the window of the outer shaft. A first electrode is disposed on the outer shaft in a region proximal along the axis to the window, and a second electrode is electrically isolated from the first electrode and disposed on the inner shaft. The second electrode is exposed in the window of the outer shaft.

23 Claims, 7 Drawing Sheets

(52) U.S. Cl.
CPC .............. *A61B 2018/00208* (2013.01); *A61B 2018/00327* (2013.01); *A61B 2018/00565* (2013.01); *A61B 2018/00595* (2013.01); *A61B 2018/00601* (2013.01); *A61B 2018/00607* (2013.01); *A61B 2218/002* (2013.01); *A61B 2218/007* (2013.01)

(58) Field of Classification Search
CPC ......... A61B 2017/320004; A61B 2018/00607; A61B 2017/22079; A61B 2017/2929; A61B 2017/320024; A61B 2017/32004; A61B 2018/1472
See application file for complete search history.

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,248,224 A | 2/1981 | Jones |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Milder |
| 5,330,521 A | 7/1994 | Cohen |
| 5,334,181 A | 8/1994 | Rubinsky et al. |
| 5,336,220 A | 8/1994 | Ryan et al. |
| 5,364,395 A | 11/1994 | West |
| 5,383,874 A | 1/1995 | Jackson et al. |
| 5,385,148 A | 1/1995 | Lesh et al. |
| 5,395,312 A | 3/1995 | Desai |
| 5,401,272 A | 3/1995 | Perkins |
| 5,405,376 A | 4/1995 | Mulier et al. |
| 5,417,709 A | 5/1995 | Slater |
| 5,431,168 A | 7/1995 | Webster, Jr. |
| 5,431,649 A | 7/1995 | Mulier et al. |
| 5,441,503 A | 8/1995 | Considine et al. |
| 5,443,463 A | 8/1995 | Stern et al. |
| 5,445,638 A | 8/1995 | Rydell et al. |
| 5,460,629 A | 10/1995 | Shlain et al. |
| 5,490,819 A | 2/1996 | Nicholas et al. |
| 5,492,527 A | 2/1996 | Glowa et al. |
| 5,496,271 A | 3/1996 | Burton et al. |
| 5,505,700 A | 4/1996 | Leone et al. |
| 5,521,576 A | 5/1996 | Collins |
| 5,540,562 A | 7/1996 | Giter |
| 5,542,196 A | 8/1996 | Hirsch et al. |
| 5,542,945 A | 8/1996 | Fritzsch |
| 5,556,397 A | 9/1996 | Long et al. |
| 5,562,702 A | 10/1996 | Huitema et al. |
| 5,569,243 A | 10/1996 | Kortenbach et al. |
| 5,573,424 A | 11/1996 | Poppe |
| 5,595,183 A | 1/1997 | Swanson et al. |
| 5,599,346 A | 2/1997 | Edwards et al. |
| 5,605,539 A | 2/1997 | Buelna et al. |
| 5,647,869 A | 7/1997 | Goble et al. |
| 5,685,838 A | 11/1997 | Peters et al. |
| 5,688,267 A | 11/1997 | Panescu et al. |
| 5,713,942 A | 2/1998 | Stern |
| 5,733,280 A | 3/1998 | Avitall |
| 5,743,903 A | 4/1998 | Stern et al. |
| 5,766,167 A | 6/1998 | Eggers et al. |
| 5,797,905 A | 8/1998 | Fleischman et al. |
| 5,797,960 A | 8/1998 | Stevens et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,873,855 A | 2/1999 | Eggers et al. |
| 5,891,142 A | 4/1999 | Eggers et al. |
| 5,895,355 A | 4/1999 | Schaer |
| 5,897,553 A | 4/1999 | Mulier |
| 5,904,681 A | 5/1999 | West, Jr. |
| 5,913,854 A | 6/1999 | Maguire et al. |
| 5,916,213 A | 6/1999 | Haissaguerre et al. |
| 5,921,982 A | 7/1999 | Lesh et al. |
| 5,925,045 A | 7/1999 | Reimels et al. |
| 5,927,284 A | 7/1999 | Borst et al. |
| 5,935,123 A | 8/1999 | Edwards et al. |
| 5,944,715 A | 8/1999 | Goble et al. |
| 5,928,191 A | 9/1999 | Houser et al. |
| 5,971,980 A | 10/1999 | Sherman |
| 5,971,983 A | 10/1999 | Lesh |
| 5,975,919 A | 11/1999 | Arnett et al. |
| 5,980,516 A | 11/1999 | Mulier et al. |
| 5,989,248 A | 11/1999 | Tu et al. |
| 5,991,650 A | 11/1999 | Swanson et al. |
| 5,993,412 A | 11/1999 | Deily et al. |
| 6,004,316 A | 12/1999 | Laufer |
| 6,004,319 A | 12/1999 | Goble et al. |
| 6,010,500 A | 1/2000 | Sherman et al. |
| 6,012,457 A | 1/2000 | Lesh |
| 6,015,391 A | 1/2000 | Rishton et al. |
| 6,024,733 A | 2/2000 | Eggers et al. |
| 6,042,556 A | 3/2000 | Beach et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,117,101 A | 9/2000 | Diederich et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,193,715 B1 * | 2/2001 | Wrublewski ....... A61B 18/1402 604/22 |
| 6,217,528 B1 | 4/2001 | Koblish et al. |
| 6,217,576 B1 | 4/2001 | Tu et al. |
| 6,221,088 B1 | 4/2001 | Bays |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,293,952 B1 | 9/2001 | Peters et al. |
| 6,293,957 B1 | 9/2001 | Peters et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,461,357 B1 | 10/2002 | Sharkey et al. |

(56) References Cited

U.S. PATENT DOCUMENTS

| | | |
|---|---|---|
| 6,468,272 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,678 B2 | 12/2002 | Sherman |
| 6,488,680 B1 | 12/2002 | Francischelli |
| 6,502,575 B1 | 1/2003 | Jacobs et al. |
| 6,503,263 B2 | 1/2003 | Adams |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,565,561 B1 | 5/2003 | Goble et al. |
| 5,697,536 A1 | 6/2003 | Eggers et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,780,180 B1 | 8/2004 | Goble et al. |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,896,674 B1 * | 5/2005 | Woloszko ........... A61B 18/1206 |
| | | 604/114 |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble et al. |
| 7,150,747 B1 | 12/2006 | McDonald et al. |
| 7,166,103 B2 | 1/2007 | Carmel et al. |
| 7,229,437 B2 | 6/2007 | Johnson et al. |
| 7,232,439 B2 | 6/2007 | Ciarrocca |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,278,994 B2 | 10/2007 | Goble |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,674,263 B2 | 3/2010 | Ryan |
| 7,691,050 B2 | 4/2010 | Gellman |
| 7,736,361 B2 | 6/2010 | Palanker |
| 7,785,337 B2 | 8/2010 | Adams et al. |
| 7,811,282 B2 | 10/2010 | McClurken |
| 7,815,634 B2 | 10/2010 | Bloom et al. |
| 7,854,736 B2 | 12/2010 | Ryan |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,012,153 B2 | 9/2011 | Woloszko et al. |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Bloom et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,317,786 B2 | 11/2012 | Dahla et al. |
| 8,323,276 B2 | 12/2012 | Palanker et al. |
| 8,348,946 B2 | 1/2013 | McClurken |
| 8,361,068 B2 | 1/2013 | McClurken |
| 8,377,086 B2 | 2/2013 | Flynn et al. |
| 8,388,642 B2 | 3/2013 | Muni et al. |
| 8,414,572 B2 | 4/2013 | Davison et al. |
| 8,688,237 B2 | 4/2014 | Stanislaus et al. |
| 9,289,141 B2 | 3/2016 | Lowery et al. |
| 2001/0007938 A1 | 7/2001 | Long |
| 2002/0038122 A1 * | 3/2002 | Peters ............... A61B 17/32002 |
| | | 606/45 |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0060862 A1 * | 3/2003 | Goble ............... A61B 17/32002 |
| | | 607/96 |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2003/0216725 A1 * | 11/2003 | Woloszko .......... A61B 18/1402 |
| | | 606/41 |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0070892 A1 * | 3/2005 | Ciarrocca ............ A61B 18/148 |
| | | 606/46 |
| 2005/0090815 A1 | 4/2005 | Francischelli |
| 2005/0090816 A1 | 4/2005 | McClurken et al. |

(56) References Cited

U.S. PATENT DOCUMENTS

| | | |
|---|---|---|
| 2005/0143729 A1 | 6/2005 | Francischelli |
| 2005/0165392 A1 | 7/2005 | Francischelli |
| 2005/0171525 A1 | 8/2005 | Rioux et al. |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0178670 A1* | 8/2006 | Woloszko ........... A61B 18/1402 606/48 |
| 2006/0200123 A1* | 9/2006 | Ryan .................. A61B 18/148 606/48 |
| 2007/0049920 A1 | 3/2007 | Bloom et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0156131 A1* | 7/2007 | Datta ................. A61B 18/1492 606/41 |
| 2007/0179495 A1 | 8/2007 | Salinas et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0207208 A1 | 8/2008 | Schutz |
| 2008/0262489 A1 | 10/2008 | Steinke |
| 2009/0118729 A1 | 5/2009 | Auth et al. |
| 2009/0264879 A1 | 10/2009 | Bloom et al. |
| 2009/0306655 A1 | 12/2009 | Stangeness |
| 2010/0087812 A1 | 4/2010 | Davison et al. |
| 2010/0100095 A1 | 4/2010 | Bloom et al. |
| 2010/0160906 A1 | 6/2010 | Jarrard |
| 2010/0241178 A1 | 9/2010 | Tilson et al. |
| 2011/0028965 A1 | 2/2011 | McClurken |
| 2011/0064978 A1* | 3/2011 | McGahan .......... A61B 17/7091 429/61 |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0165812 A1* | 6/2012 | Christian ........... A61B 18/1492 606/41 |
| 2012/0172877 A1 | 7/2012 | Ryan et al. |
| 2012/0179158 A1 | 7/2012 | Stierman |
| 2012/0184983 A1 | 7/2012 | Chang et al. |
| 2012/0191084 A1 | 7/2012 | Davison et al. |
| 2012/0191117 A1 | 7/2012 | Palmer et al. |
| 2012/0215245 A1 | 8/2012 | Palmer et al. |
| 2012/0253343 A1 | 10/2012 | McClurken et al. |
| 2013/0053830 A1 | 2/2013 | Edwards et al. |
| 2013/0085498 A1 | 4/2013 | Matusaitis et al. |
| 2013/0345704 A1 | 12/2013 | Palmer et al. |
| 2015/0173827 A1 | 6/2015 | Bloom et al. |
| 2016/0235468 A1 | 8/2016 | Prisco et al. |
| 2016/0235469 A1 | 8/2016 | Prisco et al. |
| 2016/0235474 A1 | 8/2016 | Prisco et al. |

OTHER PUBLICATIONS

Berger et al., Histopathological Changes After Coblation Inferior Turbinate Reduction, Arch Otolaryngol Head Neck Surg. 2008;134(8):819-823.

Micropen Technologies, MicroPenning, MicroPen Technologies, Sep. 13, 2010, 3 pages.

Arthrocare PROcise EZ View Sinus Wand with integrated ablation, suction, and bipolar hemostasis. 2008 (1 pg.) admitted prior art document.

* cited by examiner

ELECTROSURGICAL CUTTING INSTRUMENT

CROSS REFERENCE TO RELATED APPLICATIONS

This Non-Provisional Patent Application claims the benefit of the filing date of U.S. Provisional Patent Application Ser. No. 61/944,863, filed Feb. 26, 2014, entitled "ELECTROSURGICAL CUTTING INSTRUMENT," which is herein incorporated by reference.

BACKGROUND

The disclosure relates to instruments or tools used in performing surgery on a patient. More particularly, the disclosure relates to cutting instruments using electrodes to seal or cauterize tissue.

Clinicians use surgical instruments, including debriders such as microdebriders, to shave, cut, resect, abrade, or remove tissue, bone, or other body materials from a surgical site during surgery including endoscopic surgery. An example of such an instrument includes a rotating cutting blade on an elongated tube. The elongated tube is fit within an elongated outer tube having a cutting window exposing the cutting blade. The cutting blade is rotated within and with respect to the outer tube. The outer tube and inner tube are coupled to a handpiece. The handpiece typically includes a motor coupled to inner tube to rotate the cutting blade with respect to the handpiece. Typically, an actuator on the handpiece controls the rotation of the motor. A clinician is thus able to manipulate the location and rotation of the cutting blade to remove material from the surgical site. In some examples, a vacuum is applied through the inner tube to remove material that is cut with the blade. Many instruments also supply an irrigation fluid to the surgical site. The surgical instruments provide precise mechanical cutting at a surgical site through a low or minimally invasive incision or entry point in the patient.

An issue typically presented with surgical cutting instruments such as debriders involves the ability to control bleeding. If bleeding is not controlled, blood can obscure the view of the surgical site, adversely affect the precision of the cutting or severing tissue, and prolong the surgery. Too much blood loss can cause trauma to the patient that may require a blood transfusion. Electrosurgical instruments are often used to control bleeding in such circumstances. Electrosurgical instruments can be used to cauterize, coagulate/desiccate or simply reduce blood flow by controlling electrosurgical energy applied to the tissue. Small blood vessels, e.g., those having a diameter of less than about two millimeters, can be coapted through coagulation, i.e., the process of desiccating tissue where the tissue cells are ruptured and dried. Larger blood vessels may be coapted through sealing, i.e., the process of liquefying the collagen in the tissue so that it reforms into a fused mass. In some instances, a second surgical device is used to control bleeding either before or after body material is cut. Some electrosurgical cutting instruments include the ability to cut body material and control bleeding with the same device.

SUMMARY

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

Surgical instruments such as debriders are suitable for a variety of surgical applications including ear, nose, and throat (ENT) procedures. Sinus procedures are challenging due to the proximal location of sensitive organs such as the eyes and brain and due to the small size of the surgical site.

The disclosure is directed to debriders that provide both cutting or debridement and sealing energy through energized electrodes and fluids. The debriders conduct sealing energy to the electrode via conductive shafts selectively coated with an insulating material. The conductive shafts provide for robust electrodes as well as reduced costs and a more streamlined assembly.

In one aspect, the disclosure is directed to an electrosurgical device having a tubular outer shaft and an inner shaft. The tubular outer shaft includes an axis and a distal end region. The distal end region includes a distal-most tip and a cutting edge defining a window in the outer shaft proximal along the axis to the distal-most tip. The inner shaft inner shaft is coaxially maintained within the outer shaft such that the inner shaft is movable about the axis with respect to the outer shaft and wherein a portion of the inner shaft is exposed in the window of the outer shaft. The inner shaft includes an outer surface and an inner surface forming an axial lumen. The inner surface of the inner shaft is exposed in the window while in an open configuration and the outer surface of the inner shaft is exposed in the window while in a closed configuration. A first electrode is disposed on the outer shaft in a region proximal along the axis to the window. A second electrode electrically isolated from the first electrode and disposed on the outer surface of the inner shaft. The second electrode is exposed in the window of the outer shaft in the closed configuration, and the inner surface in the portion exposed by the window in the open configuration is covered in an electrically isolating material.

In another aspect, the disclosure is directed to an electrosurgical device having a tubular outer shaft and a tubular inner shaft. The tubular outer shaft includes an axis and a distal end region. The distal end region includes a distal-most tip and a cutting edge defining an outer shaft window proximal along the axis to the distal-most tip. The tubular inner shaft is coaxially maintained within the outer shaft such that the inner shaft is movable about the axis with respect to the outer shaft. The inner shaft includes an outer surface having a toothed edge defining an opening. The opening exposes an inner surface of the inner shaft in the window of the outer shaft when the opening is aligned with the window. A first electrode is disposed on the outer shaft in a region proximal along the axis to the window. A fluid distribution point is disposed on the outer shaft in a region proximal along the axis to the first electrode. The fluid distribution point emits fluid across the first electrode and toward the distal-most end. A second electrode electrically is isolated from the first electrode. The second electrode is disposed on the outer surface of the inner shaft and exposed in the window of the outer shaft. The second electrode includes a first portion disposed on the outer surface of the inner shaft. The inner surface of the inner shaft is covered in an electrically isolating material.

In still another aspect, the disclosure is directed to an electrosurgical system having a tubular outer shaft and a tubular inner shaft. The outer shaft includes an elongate portion and a distal end region. The distal end region includes a distal-most tip defining a window in the outer shaft proximal along the axis to the distal-most tip. The elongate portion includes a conductive shaft covered with an electrically isolating material. The distal end region is configured from an insulator. The inner shaft is coaxially maintained within the outer shaft such that the inner shaft is movable about the axis with respect to the outer shaft. A portion of the inner shaft is exposed in the window of the outer shaft, and the inner shaft is electrically isolated from the conductive shaft. The inner shaft includes an outer surface and an inner surface forming an axial lumen. The inner surface of the inner shaft is exposed in the window while in an open configuration, and the outer surface of the inner shaft is exposed in the window while in a closed configuration. A first electrode disposed on the outer shaft in a region proximal along the axis to the window and on the insulator of the distal end region. The first electrode is electrically coupled to the conductive shaft. A second electrode is disposed on the inner shaft and electrically isolated from the first electrode. The second electrode is exposed in the window of the outer shaft at least in one of the open configuration and the closed configuration.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments or examples in which the invention may be practiced. It is to be understood that other examples may be utilized and structural or logical changes may be made without departing from the scope of the present disclosure. The following detailed description, therefore, is not to be taken in a limiting sense, and the scope of the present invention is defined by the appended claims. It is to be understood that features of the various exemplary embodiments described herein may be combined with each other, unless specifically noted otherwise.

Figure 1:
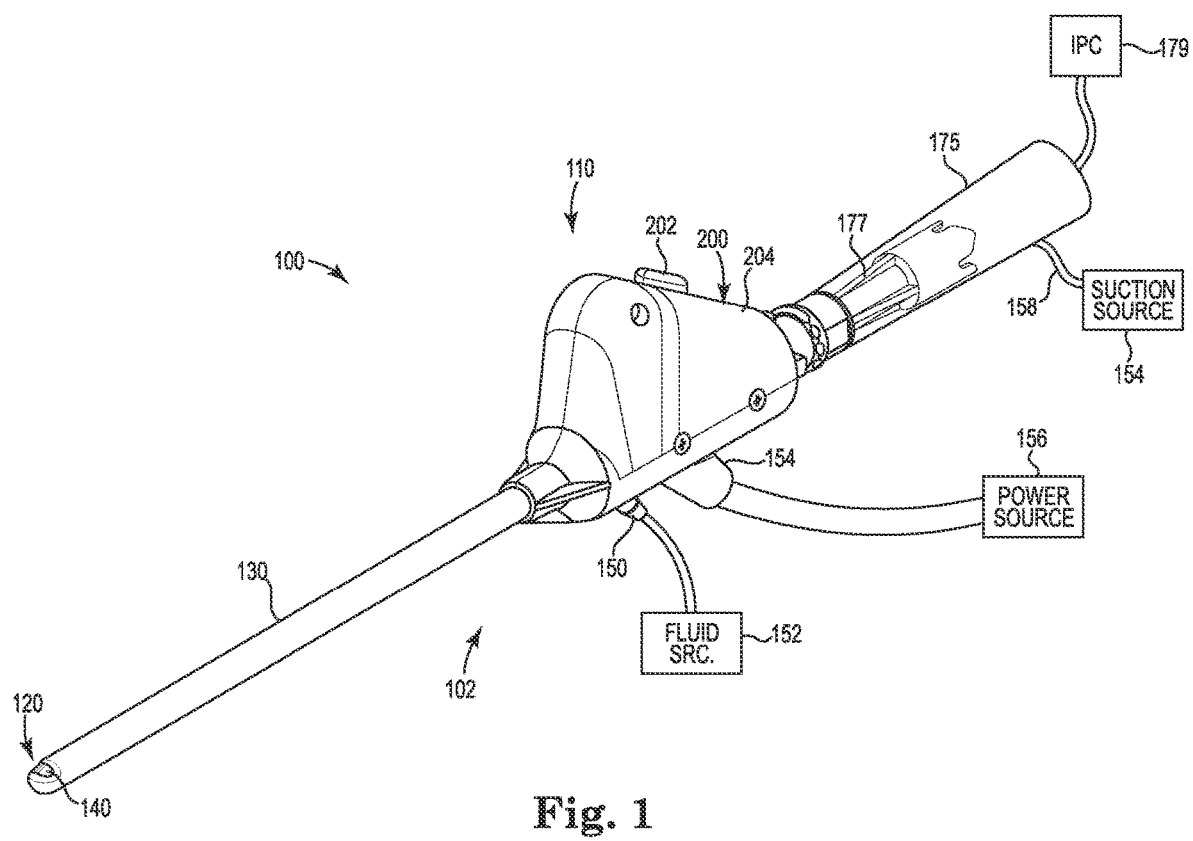
FIG. 1 is a schematic perspective view illustrating an example electrosurgical cutting instrument constructed in accordance with the present disclosure.

FIG. 1 illustrates a system 100 that includes an electrosurgical device 102 having a proximal end region 110 and a distal end region 120. The device 102 includes tubular, or hollow, outer shaft 130 and a tubular, or hollow, inner shaft 140 coaxially maintained within the outer shaft 130. The distal end region 120 is configured to engage the surgical site. A portion of the inner shaft 140 is exposed at distal end region 120. The distal end region 120 includes a mechanical cutting element, such as a blade, and a bipolar electrode to provide for coapting blood vessels during hemostasis. In one example, at least the exposed portion of the inner shaft 140 is movable with respect to the outer shaft 130 to effect mechanical cutting at the surgical site. The distal end region 120 typically includes a low profile as it is often inserted through an incision in the patient.

In the example, proximal end region 110 includes a handle or handpiece 175 and an actuator 200 remote from the distal end 120 and thus remote from the surgical site such as outside of the patient. A clinician can grasp the handpiece 175 and can control the system 100 or operate the device 102 at least in part through the actuator. The actuator 200 includes a button 202 carried on a housing 204. In the example, the handpiece 175 and the actuator housing 204 are coupled together and affixed to the outer shaft 130 such that the outer shaft does not move with respect to the handpiece 175 and actuator housing 204. Examples are contemplated, however, where the outer shaft 130 can rotate with respect to the housing 204 and inner shaft 140.

The proximal end region 110 also includes a hub 177 coupled to inner shaft 140. In the example, the hub 175 is disposed within the handpiece 175 and is configured to move the inner shaft 140 with respect to the outer shaft 130. The device 102 may be coupled to an driving mechanism or motor, which may be included as part of an integrated power console, or IPC, 179 for driving the hub 177 and specifically for controlling rotation or oscillation of inner shaft 140 with respect to the handpiece 175.

Proximal end region 110 also includes a fluid source connector 150 for connection to a fluid source 152. In one example, the fluid source 152 can include a bag of fluid coupled to flexible delivery tubing to carry the fluid to connector 150. The fluid is conveyed along the shafts 130, 140 and is emitted from an opening at the distal end region 120. The hub 177 may be made isolated from the fluid source connector through the application of a silicon O-ring disposed around the inner shaft 140 proximal to the fluid source connector 150 and distal to the hub 177 or by other mechanisms. In one example, the fluid includes saline and can include physiologic saline such as sodium chloride (NaCl) 0.9% solution. Saline is an electrically conductive fluid, and other suitable electrically conductive fluids can be used. In other examples, the fluid may include a nonconductive fluid, such as deionized water, which may still provide advantages over using no fluid.

A pump can be used to convey fluid to the electrosurgical device 102 and control fluid flow. In one example, delivery tubing is passed through pump. Pump in one example is a peristaltic pump such as a rotary peristaltic pump or a linear peristaltic pump. Pump can convey the fluid through the delivery tubing by way of intermittent forces placed on the external surface of the delivery tubing. Peristaltic pumps are often preferred because the mechanical elements of the pump places forces are placed on the external surface of the delivery tubing and do not come into direct contact with the fluid, which can reduce the likelihood of fluid contamination. Other examples of system 100 might not include a pump, and fluid can be is provided to the electrosurgical device 102 via gravity.

Proximal end region 110 also includes a power source connector 154 for connection to a source of electrical energy indicated as power source 156. Power source 156 provides electrical energy, such as radio-frequency (RF) energy via insulated wires to the power source connector 154. The power source connector 154 is in electrical communication with conductors along the elongated portions of the shafts 130, 140 to bipolar electrodes at the distal end region 120. In the example, the conductive outer shaft 130 is configured to carry RF energy to an electrode at a first pole and the conductive inner shaft 140 is configured to carry RF energy to an electrode. The first and second poles are opposite from each other, such as the first pole is active and the second pole is passive, and the outer shaft 130 and inner shaft 140 are electrically isolated from each other.

In one example, the elongated portions of the outer and inner shafts 130, 140 are conductive themselves and carry the RF energy from the power source 156 to electrodes at the distal end region 120. In the example shown, the conductive portion of the outer shaft 130 is covered with an elongate insulator 131 that extends from at least the proximal end region 110 to at least the distal end region 120. Accordingly, the elongated portion of outer shaft 130 conveys RF energy from the power source connector 154 to the distal end region 120, but is insulated from any articles that may come into contact with the elongated portion of the outer shaft 130.

In one example of power source 156 includes a generator configured for use with one or more electrosurgical devices. An example generator is available under the trade designation Aquamantys and provides a type of RF sealing energy technology available under the trade designation Transcollation from Medtronic Advanced Energy of Portsmouth, N.H., United States. Examples of suitable generators and flow rate controllers are described in U.S. Pat. No. 7,815,634, and published U.S. Pat. Application Nos. 2001-0032002; 2006-0149225 and 2005-0090816, which are incorporated by reference into this disclosure.

Proximal end region can also include a suction source connector 158 for connection to a suction source 159. The suction connector 158 is in fluid communication with an opening in the distal end region 120. Fragments of body materials cut with the device 102 and fluids can be removed from the surgical site through the opening in the distal end region via the suction source 159.

Figure 2:
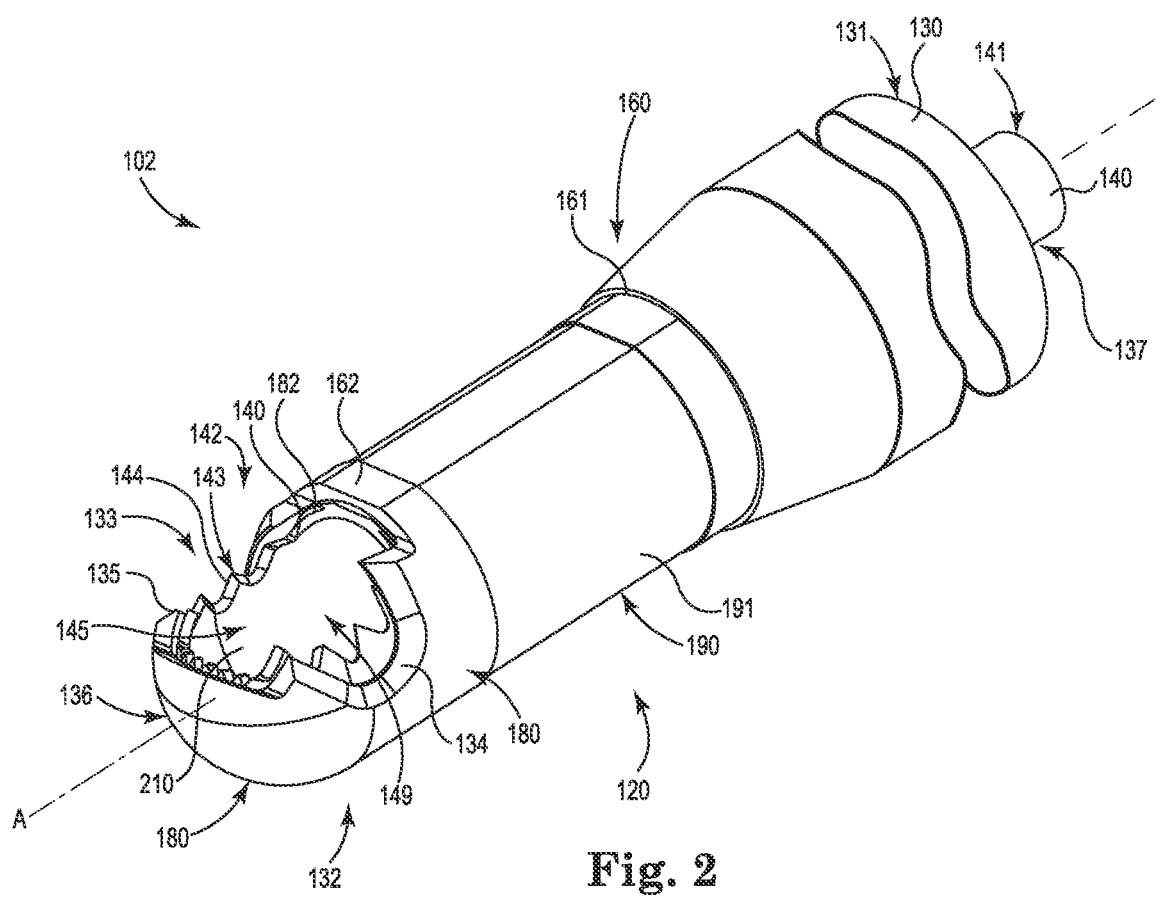
FIG. 2 is a schematic perspective view illustrating an example distal portion of the electrosurgical cutting instrument of FIG. 1 in a first configuration.
Figure 3:
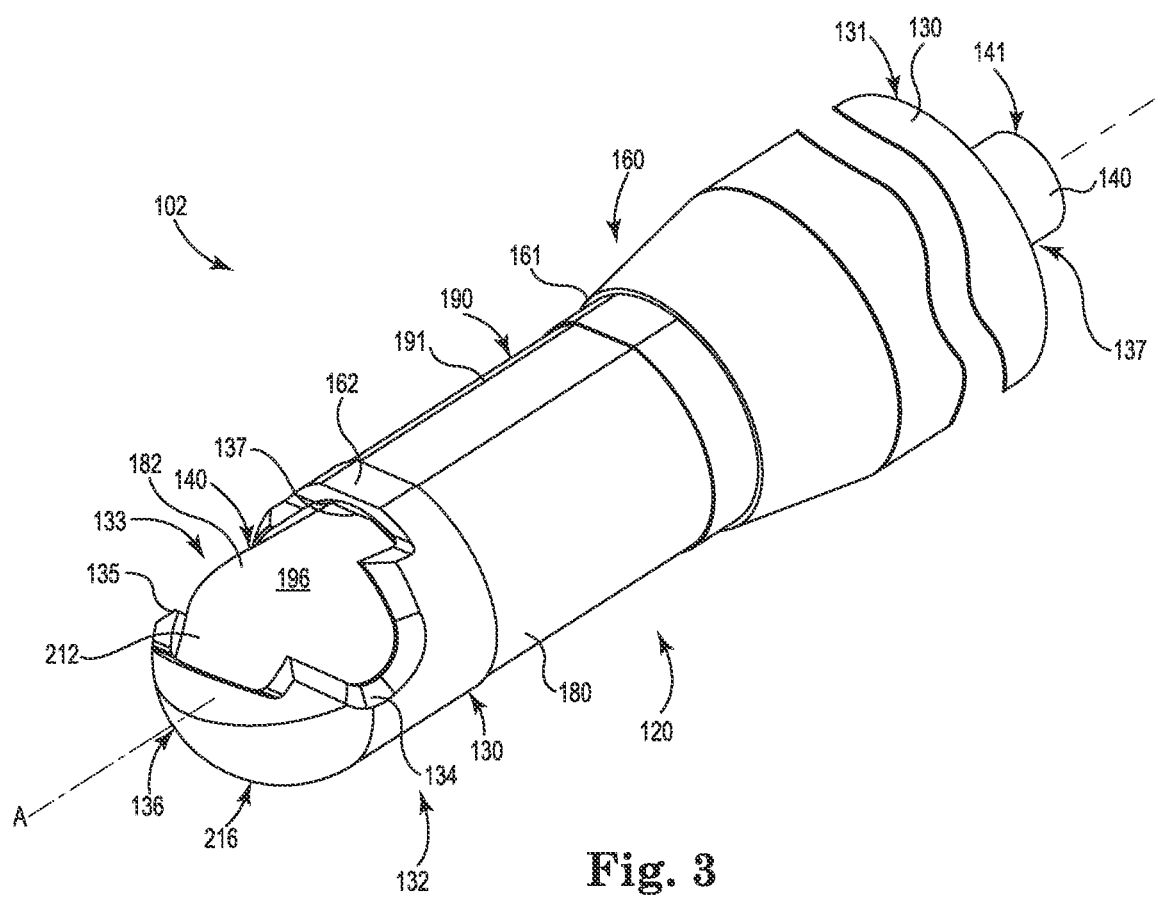
FIG. 3 is a schematic perspective view illustrating an example distal portion of the electrosurgical cutting instrument of FIG. 1 in a second configuration that is different than the first configuration.

FIGS. 2 and 3 illustrate schematic perspective views of outer shaft 130 and inner shaft 140 of device 102 in different configurations. In particular, FIG. 2 illustrates the device 102 with inner shaft 140 in a first configuration with respect to outer shaft 130. FIG. 3 illustrates the device 102 with inner shaft 140 in a second configuration with respect to outer shaft 140.

FIGS. 2 and 3 illustrate elongated inner shaft 140 coaxially maintained within elongated outer shaft 130 along axis A. The outer shaft 130 includes an elongated portion that extends from a proximal end 131, which can be connected to housing 204, to a distal end 132 that includes an opening such as window 133 and a distal-most tip 136. An outer shaft cutting edge 134 defines window 133. In the example, the outer shaft cutting edge 134 includes cutting teeth 135. The outer shaft 130 may be rigid, malleable, or include combinations including a rigid portion and a malleable portion.

The inner shaft 140 includes an elongated portion that extends from a proximal end 141, which can be connected to hub 177, to a distal end 142. A portion of the distal end 142 is exposed to the surgical site through window 133 of outer shaft 130.

A lumen 137 formed between the outer shaft 130 and the inner shaft 140 is configured to carry fluid between an outer surface of the inner shaft 140 and an inner surface of the outer shaft 130. Fluid is emitted from the distal end region 120 at distribution point 160. In one example, the outer shaft 130 includes more than one distribution points, such as proximal distribution point 161 and distal distribution point 162 that are spaced-apart from each other. In the example, distribution points 161 and 162 are aligned along longitudinal axis A on the outer surface 180 of the outer shaft 130. Fluid from distribution point 161, as well as distribution point 162, generally flows axially along the outer surface 180 towards window 133 of the outer shaft 130.

One or more outer shaft electrodes 190 can be disposed along the outer surface 180 of the outer shaft 130 in the distal end region 120. In the example design illustrated in FIG. 2, an electrode 191 is exposed on the outer surface 180 of the outer shaft 130 between fluid distribution point 161 and the window 133 of the outer shaft 130 in the path of fluid flow. More particularly, the electrode 191 can be exposed on the outer surface 180 between proximate fluid distribution point 161 and distal distribution point 162. The remaining portions of the outer surface 180 in the distal end region can be covered with an insulator or electrically isolating material 216. The electrode 191 can be formed as a patch of a conductive element in electrical communication with the power source connector 154 partially extending around the outer surface 180 or, as illustrated, a conductive element along the entire circumference of the outer surface 180 between the distribution point 161 and window 133.

In one example, electrode 191 can be an exposed portion of the conductive portion of the outer shaft 130, i.e., a portion of the outer shaft 130 without an electrically isolating coating 216, rather than a separate conductor affixed to the outer shaft 130. Electrode 191 is thus in electrical communication with the power source connector 154.

FIG. 2 also illustrates inner shaft 140 in a first configuration, or open position, with respect to outer shaft 130 such that an inner shaft cutting edge or inner cutter 143 is exposed to window 133. Inner cutter 143 includes cutting teeth 144 and defines an inner shaft window or opening 145. An inner surface 182 of the inner shaft 140 is exposed to the surgical site in the open position. The inner surface 182 defines a lumen 149 axially extending along the elongated inner shaft 140. Fluid from distribution point 161 and distribution point 162 can collect on the inner surface 182 of the inner shaft 140 within lumen 149.

The device 102 can be used to remove body matter and fluids from the surgical site while the outer and inner shaft cutters 134 and 143 are the open position. For example, the inner shaft and outer shaft cutters 134, 143, respectively, may move relative to one another in oscillation, rotation, or both, via the hub 177 to mechanically cut body matter. In one example, outer shaft cutter 134 may remain stationary relative to the handpiece 175 and actuator housing 204 while the inner shaft cutter 143 rotates about longitudinal axis A of the device to cut body matter. Also, the outer shaft 130 and the inner shaft 140 can be locked in the open position. The clinician can also manipulate the device 102 so that the distal end region moves along the longitudinal axis A, rotates about the longitudinal axis A, or otherwise to cut body matter with teeth 144 without rotating the inner shaft 140 with respect to the outer shaft 130.

The inner shaft opening 145 is fluidly connected to an inner shaft lumen 149 that extends from the inner shaft opening 145 to the proximal end 141 of inner shaft 140 and may be fluidly connected with the suction source 159 through suction source connection 158. When the inner shaft 130 is in the open position, body matter cut via inner and outer shaft cutters 143, 134 and fluid, such as fluid emitted from distribution points 161 and 162 is aspirated into the inner shaft lumen 149 through the inner shaft opening 145 upon application of suction source 159 to remove body material and fluid from the surgical site.

In the illustrated example of FIG. 2, the inner surface 182 of the inner shaft is covered in an insulator 210 to electrically isolate the electrode 191 from the conductive portions of the inner shaft 140. In this example, the inner shaft does not include an electrode and the distal end region 120 does not deliver RF energy to the tissues when the inner shaft 140 is in the open configuration relative to the outer shaft 130.

In other examples, the inner surface 182 of the inner shaft 140 can include one or more inner surface electrodes in the distal end region 120. For example, an inner surface electrode can be formed with the conductive portion of the inner shaft 140 is exposed on the inner surface 182 in a region axially distal to the distal fluid distribution point 162 on the outer surface 180 of the outer shaft 130. In another example, an inner surface electrode can be formed with conductive portion of the inner shaft 140 exposed on inner surface 182 of the inner shaft 140 in the region at least distal to the proximal-most inner shaft edge 143 or proximal-most portion of the inner shaft window 145. An inner surface electrode would be electrically isolated from the outer shaft electrode 191. In this example, an inner surface electrode is in electrical communication with the power source connector 154 and forms an electrode pole opposite the pole of the outer surface electrode 191. For example, if the outer surface electrode 191 is the active electrode then an inner surface electrode is the return electrode in the bipolar configuration.

FIG. 3 illustrates the inner shaft 140 in a second configuration, or closed position, with respect to the outer shaft 130. An outer surface 184 of the inner shaft 140 is exposed in outer shaft window 133 of the outer shaft 130. Inner shaft 140 is rotated about longitudinal axis A within the outer shaft 130 such that the inner shaft cutter 143 is completely shielded from exposure. For example, the inner shaft in the closed position can be rotated 180 degrees with respect to inner shaft relative to the outer shaft in the open position. The inner shaft cutter 143 in one example, is facing the interior of the outer shaft 130 opposite from the outer shaft window 133 and an outer surface 184 of the inner shaft 140 is exposed in the window 133. In some examples, the longitudinal edges of window 133 do not extend 180 degrees radially around the circumference of the outer shaft 130. In this case, the inner shaft 140 can be rotated less than 180 degrees from the open position to be in the closed position. In one example, the inner shaft 140 can be locked in the closed position.

One or more electrodes, such as electrode 196, can be disposed on the outer surface 184 of the inner shaft 140. In the example, electrode 196 is exposed in the window 133 while the inner shaft 140 is in the closed position. In the example, electrode 196 is exposed on the outer surface 184 of the inner shaft 140 in the region axially distal to the distal fluid distribution point 162 on the outer surface 180 of the outer shaft 130. In another example, the electrode 196 is exposed on outer surface 184 of the inner shaft 140 in the region at least longitudinally distal to the proximal-most inner shaft edge 143 or proximal-most portion of the inner shaft window 145.

In one example, the outer surface 184 of the inner shaft 140 is an electrically isolating material 212 covering the conductive portion. In this example, electrode 196 can be an exposed portion of the conductive portion of the inner shaft 140, i.e., a portion of the inner shaft 140 without an electrically isolating coating, rather than a separate conductor affixed to the inner shaft 140. Electrode 196 is thus in electrical communication with the power source connector 154.

Electrode 196 is electrically isolated from the outer shaft electrode 190, such as electrode 191. Electrode 196 forms an electrode pole opposite the pole of the outer surface electrode 190. For example, if the outer surface electrode 190 on the outer shaft 130 is the active electrode then the electrode 196 on the inner shaft 140 is the return electrode in the bipolar configuration.

If the inner shaft 140 also includes an inner surface electrode, the electrode 196 on the outer surface 184 can be made to be in electrical communication with the electrode on the inner surface 182 of the inner shaft 140.

Energized electrodes 191 and 196 along with fluid dispersed from distribution points 161 and 162 combine to form a field of RF energy to coapt blood vessels during hemostasis. In one example, RF energy is delivered to tissue through electrodes 191, 196 while the inner shaft 140 is in the closed position without attendant risk that the cutting teeth 144 of the inner shaft 140 will diminish the efforts to achieve hemostasis. Device 102 may thus comprise two modes: a cutting or debridement mode and a sealing or hemostasis mode and the two modes may be mutually exclusive. In other words, hemostasis is achieved via RF energy delivered to tissue while cutters 134, 143 are not active or cutting. Further, RF energy may be advantageously delivered simultaneously with the fluid such as saline to achieve an optimal tissue effect by delivering controlled thermal energy to tissue.

In other examples, RF energy may be delivered to electrodes during cutting mode while the cutters 134, 143 are actively cutting so that cutting or debridement mode is not exclusive of sealing or hemostasis mode. Still further, the inner shaft 140 may be locked in an open position during sealing or hemostasis mode in order for fluid to collect and be suctioned from lumen 149 in case the inner surface 182 includes an electrode.

Figure 4:
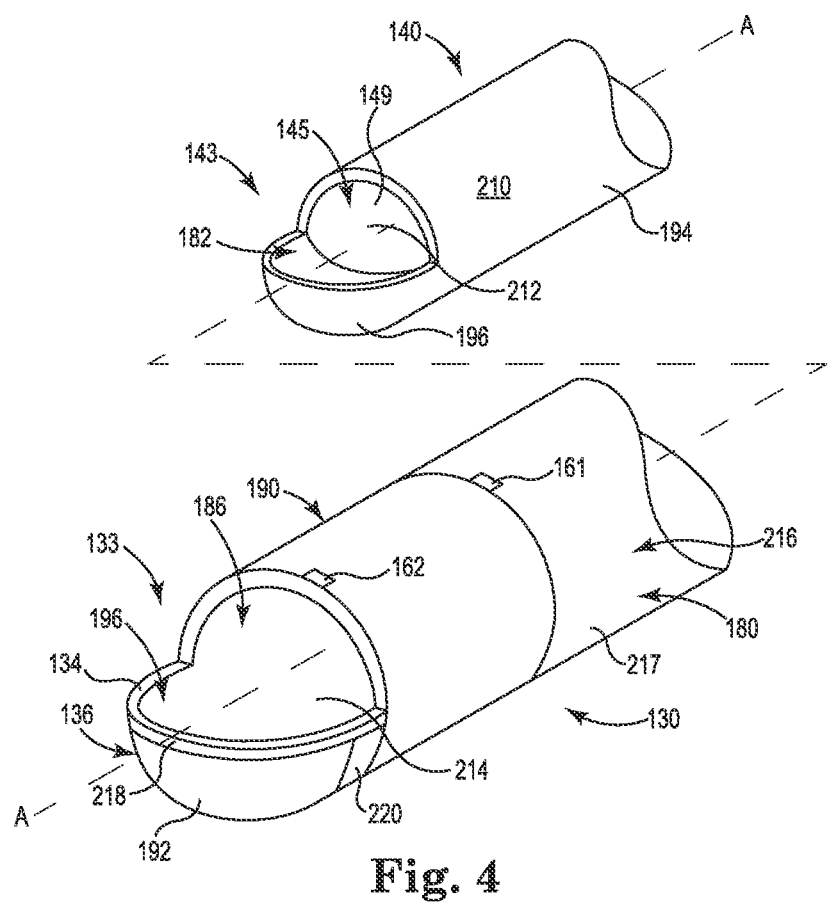
FIG. 4 is schematic exploded view illustrating features of components of the electrosurgical cutting instrument of FIG. 1.

FIG. 4 schematically illustrates outer shaft 130 and inner shaft 140 in the design illustrated in FIGS. 2 and 3. Inner shaft 140 includes inner cutter 143 defining inner shaft opening 145, as illustrated schematically. Inner shaft 140 also includes inner surface 182 forming lumen 149 and outer surface 184. The inner shaft 140 is formed from a conducting material that is covered with an electrically isolating coating, or insulator. The inner surface 182 is covered in the insulator 210 at least at the distal tip region 120. The insulator 212 on the outer surface 184 of the inner shaft 140 is formed to expose outer surface electrode 196.

Outer shaft 130 includes distal-most tip 136 and cutting edge 134 to define window 133, also as illustrated schematically. Outer shaft 130 also includes outer surface 180 and, as illustrated, inner surface 186 forming lumen 139. The outer shaft 130 is formed from a conductive material that is covered with an electrically isolating coating, or insulator 216 on the outer surface 180. The inner surface 186 is covered in the insulator 214 at least at the distal tip region 120. The insulator 216 on the outer surface 180 of the outer shaft 130 is formed to expose outer surface electrode 191.

Inner and outer shafts 130 and 140 are preferably constructed from a metal such as titanium, copper, tantalum, molybdenum, tungsten, or stainless steel, or another conductive material that can withstand forces used to cut body materials and repeated sterilizations in high temperature autoclaves or other suitable medical-grade materials. If the shafts 130, 140 are intended for single use, shafts 130, 140 can be constructed from a conductive medical-grade material that can withstand forces used to cut body materials and temperatures used in hemostasis.

The inner shaft 140 is electrically isolated from the outer shaft 130. This can include forming an insulator on the entire outer surface 184 of the inner shaft 140 (except for the exposed portion for electrode 196), the entire inner surface 186 of the outer shaft 130, both the inner surface 186 of the outer shaft 130 and the outer surface 184 of the inner shaft 140 (except for the exposed portion for electrode 196), or some other suitable combination.

Insulators 210 and 212 selectively cover the inner and outer surfaces 182, 184 of the inner shaft 140, respectively, except for the exposed portion for electrode 196. An insulator 214 selectively covers the inner surface 186 of the outer shaft 130.

Insulator 216 selectively covers the outer surface 180 of the outer shaft 130. In the example where electrode 190 extends along the entire circumference of the outer surface 180, insulator 216 can include insulators 217 and 218 selectively to cover separate regions of the outer surface 180 of the outer shaft 130. For example, insulator 217 covers the elongate portion of the outer surface 180 of the outer shaft 130, and insulator 218 covers the distal tip 136 of the outer shaft 130.

Insulators 210, 212, 214, 216 can be one or more medical-grade insulating polymer formed from fluorinated ethylene propylene (FEP), polytetrafluoroethylene (PTFE), parylene or any other material suitable as a non-conductive or electrically insulative material. In one example, the coating includes polyaryletherketones (PAEK) polymer thermoplastic such as polyetheretherketone (PEEK) polymer thermoplastic. One particularly suitable and medical-grade PEEK polymer thermoplastic coating is available under the trade designation Vicote from Victrex Manufacturing Ltd. of Thorton Cleveleys, Lancashire, United Kingdom. The polymer thermoplastic can be dispersed on the conductors of portions of shafts 130 and as either a powder or aqueous solution to form coatings for surfaces 180, 182, 184, and 186. The insulator is capable of withstanding use and cleaning conditions.

Electrodes, such as electrodes 191 and 196, are formed on the outer and inner shafts 130, 140. In one example, the conductive portions of shafts 130, 140 are masked while the insulators are being coated on the shafts, the masks are later removed to expose uncoated regions of the shafts 130, 140 configured to act as electrodes 191 and 196. In another example, the shafts 130, 140 are coated, and the coating is later removed from shafts 130, 140 to exposed the regions configured to act as electrodes. Still further, some combination of masking and coating removal is used to form the not coated regions configured to act as electrodes.

Figure 5:
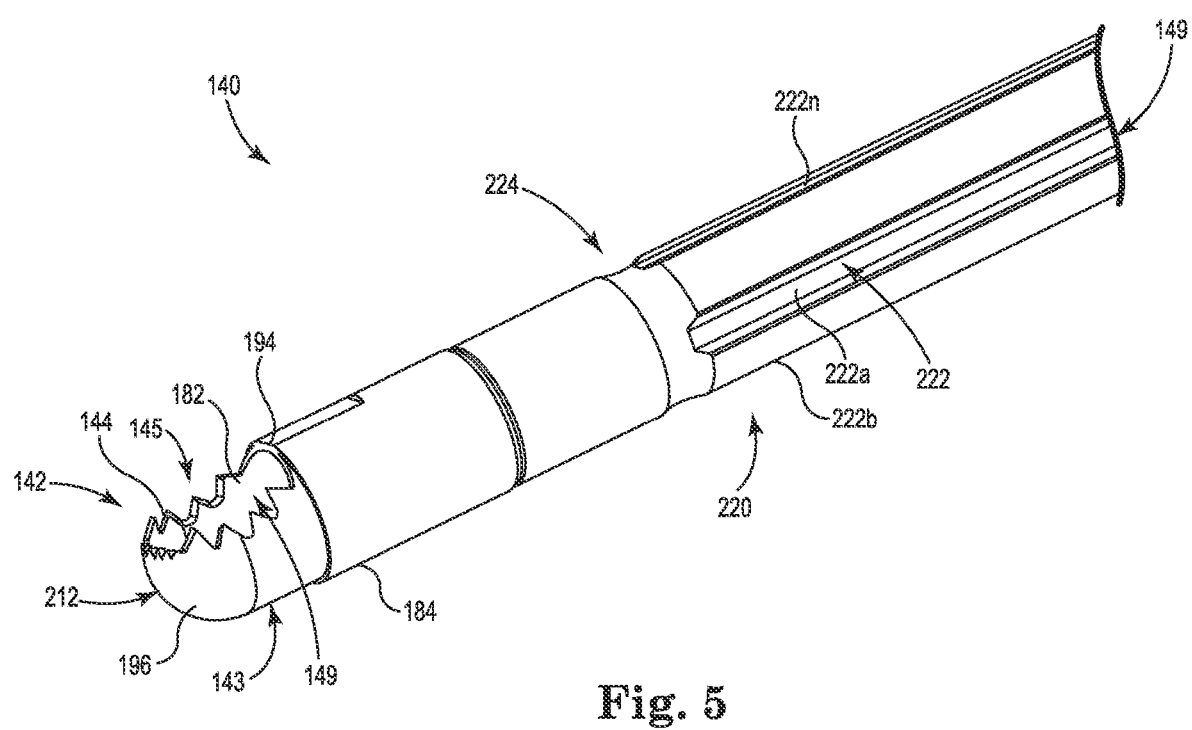
FIG. 5 is a schematic view illustrating another feature a component of the electrosurgical cutting instrument of FIG. 1.

FIG. 5 shows another schematic view of an example of the inner shaft 140. The inner shaft 130 of the example includes an insulated elongated portion 220 and an exposed and not coated inner cutter 143. The elongated portion 220 includes at least one fluid distribution flute 222 formed in the outer surface 184. The example shows a plurality of fluid distribution flutes 222a, 222b, . . . 222n formed into the inner shaft 140 and spaced-apart from each other around the circumference of the outer surface 184. At least one reservoir 224 is formed into outer surface 184 the inner shaft 140 and connected to the fluid distribution flutes 222a, 222b, . . . 222n as illustrated. In the example, reservoir 224 extends along the circumference of the outer surface 184.

Fluid collected from the reservoir can be dispersed from distribution points 161 and 162 on the outer shaft 130. When the inner shaft 140 is disposed within outer shaft 130, the inner surface 186 of outer shaft 130 combine with distribution flutes 222a, 222b, . . . 222n and reservoir to form lumen 137 described above with respect to FIGS. 2 and 3. In another example, detents can be formed in the inner surface 186 of outer shaft 130 in addition to or instead of distribution flutes 222 and reservoir 224 to form lumen 137. If detents are formed into the inner surface 186 of outer shaft 130, the outer surface 184 of inner shaft 140 can optionally be made smooth.

Figure 6:
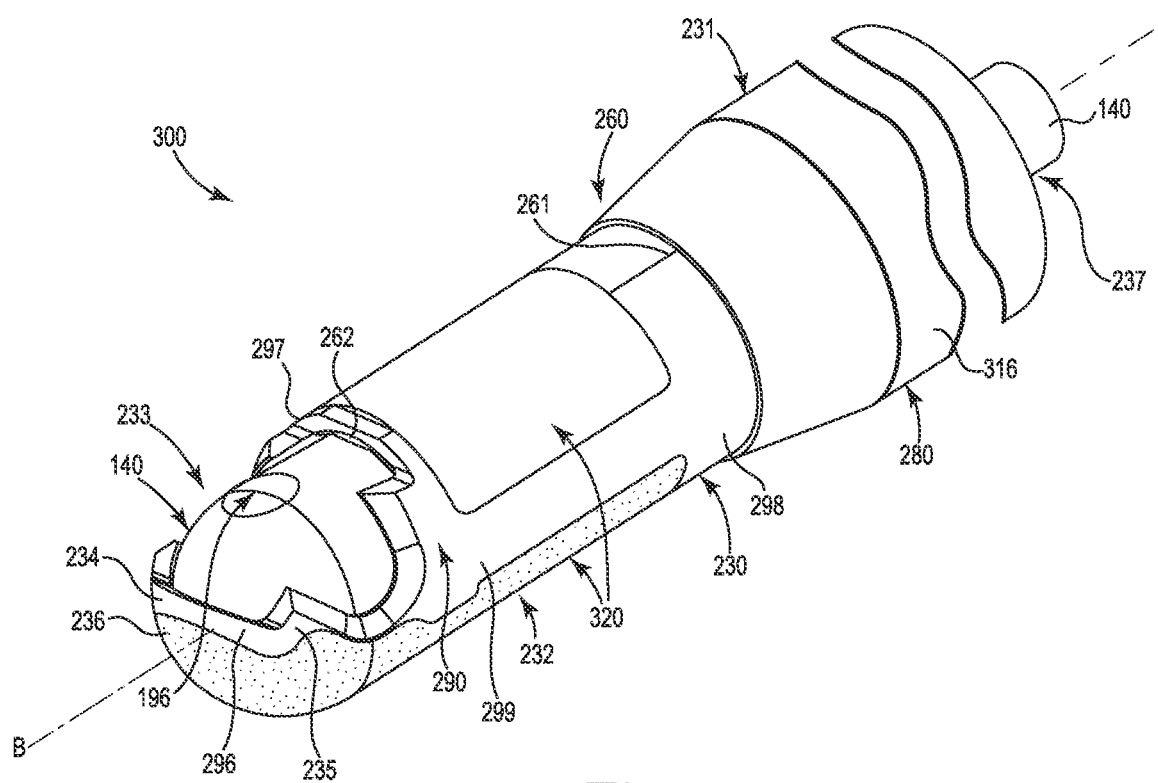
FIG. 6 is a schematic perspective view illustrating an example distal portion of an electrosurgical cutting instrument having an alternatively designed outer shaft in combination with the inner shaft in the second configuration.

FIG. 6 shows an alternative design of surgical device 102, i.e., surgical device 300. Device 300 includes an outer shaft 230, which is an alternate design of the outer shaft 130 of FIGS. 2-3. The remaining portions of device 300 can be similar to the device illustrated in FIG. 1, and like parts are labeled with like reference numerals. Device 300 includes elongated inner shaft 140, which can be the same as illustrated above, coaxially maintained within elongated outer shaft 230 along axis B. The outer shaft 230 includes an elongated portion 231 that extends from a proximal end, not shown, which can be connected to housing 204, and a distal end 232 that includes an opening such as window 233 and a distal-most tip 236. An outer shaft cutting edge 234 defines window 233. In the example, the outer shaft cutting edge 234 includes cutting teeth 235. The outer shaft 230 may be rigid, malleable, or include combinations including a rigid portion and a malleable portion. The outer surface 280 of elongated portion 231 of the outer shaft 230 can be covered in an electrically isolating material 316.

A lumen 237 formed between the outer shaft 230 and the inner shaft 140 is configured to carry fluid between an outer surface of the inner shaft 140 and an inner surface of the outer shaft 230. Fluid is emitted from the distal end region at distribution point 260. In one example, the outer shaft 230 includes more than one distribution points, such as proximal distribution point 261 and distal distribution point 262 that are spaced-apart from each other. In the example, distribution points 261 and 262 are aligned along longitudinal axis B on the outer surface 280 of the outer shaft 230. Fluid from distribution point 261, as well as distribution point 262, generally flows axially along the outer surface 280 towards window 233 of the outer shaft 230.

The outer surface 280 of distal end 232 can include an electrically isolating over-mold portion 320. In one example, the over-mold portion 320 forms the shaft 230 at the distal end 232. In particular, the over-mold portion 320 takes the place of the insulator-covered conductor at the tip in of outer shaft 130 in FIG. 4. Accordingly, the conductive elongate portion of outer shaft 230 is attached to an electrically isolating over-mold 320 to form the distal end 232. This design electrically isolates the distal end 232 from the inner shaft 140.

The electrically isolating material used to form the over-mold portion 320 can include one or more medical grade polymers, such as the medical grade polymers described above used to form insulators 210, 212, 214, 216. In one example, the over mold portion 320 is constructed from medical-grade PEEK polymer thermoplastic coating is available under the trade designation Vicote from Victrex, as described above.

Outer shaft 230 also includes an electrode 290 disposed on the electrically isolating over-mold portion 320. In one example, the electrode 290 can be formed as a sleeve prior to coupling to the outer shaft 230. The electrode 290 can be attached to the conductive portion of the shaft 230 to be in electrical communication with the power source connection 154. The electrode 290 sleeve can be attached over the over-mold portion 320. In one example, the electrode 290 can be attached directly to the conductive portion of the shaft 230 or to the conductive portion via an electrical conductor such as a wire or trace (not shown).

Electrode 290 is preferably constructed from a metal such as titanium, copper, tantalum, molybdenum, tungsten, or stainless steel, or another conductive material that can withstand forces used to cut body materials and repeated sterilizations in high temperature autoclaves or other suitable medical-grade materials. If the debrider 300 is intended for single use, electrode 290 can be constructed from a conductive medical-grade material that can withstand forces used to cut body materials and temperatures used in hemostasis.

The electrode 290 can receive RF energy and function in the same manner as electrode 190 in FIG. 2. The electrode 290 can be energized along with electrode 196 of the inner shaft 140, and fluid can be dispersed from fluid distribution points 261 and 262, to provide hemostasis at the distal end 232 as described above with respect to the design shown in FIGS. 2 and 3.

Figure 7:
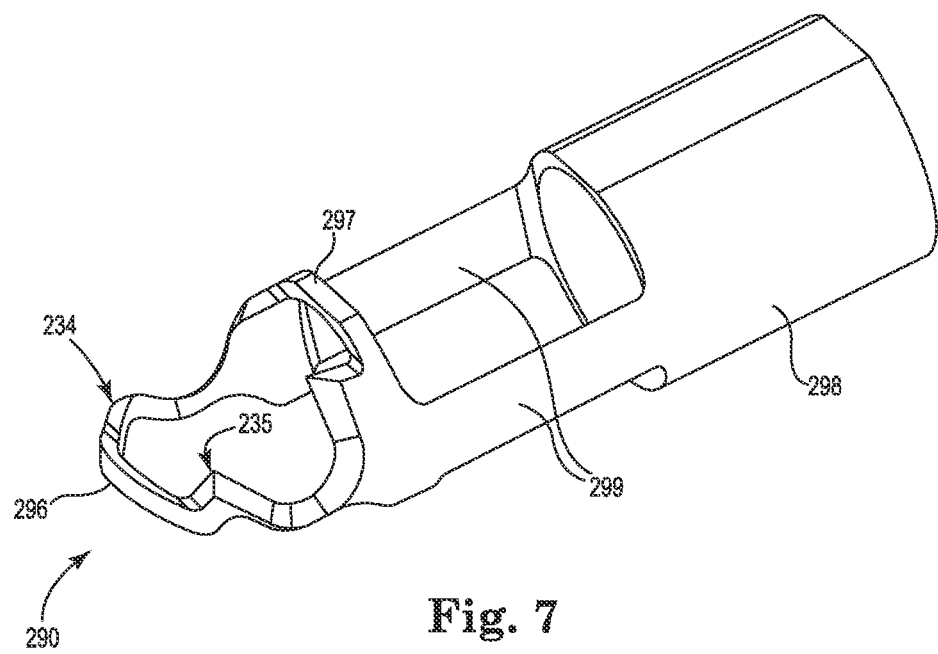
FIG. 7 is a schematic perspective view illustrating a feature of the alternately designed outer shaft of the electrosurgical cutting instrument of FIG. 6.

FIG. 7 illustrates the electrode 290 in greater detail. The electrode 290 can be wire cut to form the outer shaft cutting edge 234 including cutting teeth 235 and a distal lateral band 296. Electrode 290 can also include a distal circumferential band 297 that can extend all or partially around the circumference of the outer shaft 230 proximal to fluid distribution point 262. The distal circumferential band 297 in the example is coupled to a proximal circumferential band 298 via one or more longitudinal strips 299 configured to run axially along the over-mold portion 320. The example illustrates two longitudinal strips 299 on opposite sides of the over-mold portion 320 and, in the example, spaced-apart from the fluid distribution points 262. The proximal circumferential band 298 is configured to interface with the elongate portion of the outer shaft 230. The proximal circumferential band 298 in the example encircles the over-mold portion 320 and is configured to be distal to fluid distribution point 261.

Fluid from distribution point 261, as well as distribution point 262, generally flows axially along the outer surface 280 towards window 233 and distal tip 236 of the outer shaft 230. The fluid flows across the proximal circumferential band 298 and the distal circumferential band 296, such as fluid from distribution point 261. Additionally, fluid from distribution points 261, 262 can flow across the distal lateral band 296. The fluid is energized when the electrodes 290 and 194 are activated with RF sealing energy to create an RF field in the area near the distal region 232.

Although the present disclosure has been described with reference to preferred embodiments, workers skilled in the art will recognize that changes can be made in form and detail without departing from the spirit and scope of the present disclosure.

What is claimed is:

1. An electrosurgical device, comprising:
a tubular outer shaft having an axis, an exposed outer surface of the outer shaft, and a distal end region; wherein the distal end region includes a distal-most tip and a cutting edge defining a window in the outer shaft proximal along the axis to the distal-most tip;
an inner shaft coaxially maintained within the outer shaft such that the inner shaft is movable about the axis with respect to the outer shaft and wherein a portion of the inner shaft is exposed in the window of the outer shaft;
wherein the inner shaft includes an outer surface of the inner shaft and an inner surface of the inner shaft, the inner surface of the inner shaft forming an axial lumen, wherein the inner surface of the inner shaft is exposed in the window while in an open configuration and the outer surface of the inner shaft is exposed in the window while in a closed configuration;
an exposed first electrode disposed on the outer surface of the outer shaft in a region proximal along the axis to the window;
an exposed fluid distribution outlet port configured to disperse a fluid, the exposed fluid distribution outlet port on the outer surface of the outer shaft in a region proximal along the axis to the exposed first electrode, the exposed fluid distribution outlet port configured to direct the dispersed fluid along the outer surface of the outer shaft onto the exposed first electrode and toward the distal-most tip; and
a second electrode electrically isolated from the exposed first electrode and disposed on the outer surface of the inner shaft; wherein the second electrode is exposed in the window of the outer shaft in the closed configuration, and wherein the inner surface in the portion exposed by the window in the open configuration is covered in an electrically isolating material;
wherein the device is configured such that the second electrode is covered and not exposed in the open configuration.

2. The electrosurgical device of claim 1 wherein the outer shaft and inner shaft are configured from a conductive material.

3. The electrosurgical device of claim 2 wherein the conductive material is titanium, copper, tantalum, molybdenum, tungsten, or stainless steel.

4. The electrosurgical device of claim 2 wherein the outer and inner shaft are coated with an electrically insulating material such that the outer and inner shafts are electrically isolated from each other.

5. The electrosurgical device of claim 4 wherein the exposed first electrode is formed of conductive material exposed on the outer shaft and the second electrode is formed of conductive material exposed on the inner shaft.

6. The electrosurgical device of claim 4 wherein the electrically insulating material includes a polymer thermoplastic.

7. The electrosurgical device of claim 6 wherein the electrically insulating material is a polyaryletherketones (PAEK) polymer thermoplastic.

8. The electrosurgical device of claim 7 wherein the electrically insulating material is polyetheretherketone (PEEK) polymer thermoplastic.

9. The electrosurgical device of claim 1 comprising a second fluid distribution outlet port on the outer shaft in a region distal along the axis to the exposed first electrode.

10. The electrosurgical device of claim 1 wherein the exposed fluid distribution outlet port is in fluid communication with a lumen formed between the outer shaft and the inner shaft.

11. An electrosurgical device, comprising:
a tubular outer shaft having an axis, an exposed outer surface of the outer shaft, and a distal end region, wherein the distal end region includes a distal-most tip and a cutting edge defining an outer shaft window proximal along the axis to the distal-most tip;
a tubular inner shaft coaxially maintained within the outer shaft such that the inner shaft is movable about the axis with respect to the outer shaft and wherein the inner shaft includes an outer surface of the inner shaft having a toothed edge defining an opening, wherein the opening exposes an inner surface of the inner shaft in the window of the outer shaft when the opening is aligned with the window;
an exposed first electrode disposed on a first region of the outer surface of the outer shaft, the first region proximal along the axis to the window and the first region having a first radius of the outer surface of the outer shaft;
an exposed fluid distribution outlet disposed on a second region of the outer shaft, the second region proximal along the axis to the exposed first electrode and the second region having a second radius of the outer surface of the outer shaft greater than the first radius, the exposed fluid distribution outlet configured to emit fluid across the exposed first electrode and toward the distal-most end; and
a second electrode electrically isolated from the exposed first electrode, the second electrode disposed on the outer surface of the inner shaft and exposed in the window of the outer shaft, wherein the inner surface of the inner shaft is covered in an electrically isolating material;
wherein the outer surface of the inner shaft and an inner surface of the outer shaft define a lumen in fluid communication with the exposed fluid distribution outlet for delivering fluid to the exposed fluid distribution outlet outlet via the lumen.

12. The electrosurgical device of claim 11 wherein the inner surface of the inner shaft forms a lumen configured to be in fluid communication with a suction source.

13. The electrosurgical device of claim 11 wherein the lumen includes an axial distribution flute and a reservoir in the distal end region.

14. The electrosurgical device of claim 13 wherein the axial distribution flute is formed into the outer surface of the inner shaft, and further wherein the reservoir is formed as a circumferential groove in the outer surface of the inner shaft.

15. The electrosurgical device of claim 11 wherein the exposed first electrode is in electrical communication with an electrode surface on the outer surface of the outer shaft distal to the exposed first electrode and electrically isolated from the cutting edge.

16. The electrosurgical device of claim 11 wherein the inner shaft and outer shaft are formed from a conductive material and are coated with an electrically insulating material, wherein the exposed first electrode and the second electrode are exposed and uncoated regions of the outer and inner shafts.

17. An electrosurgical device, comprising:
a tubular outer shaft having an axis, an elongate portion, an exposed outer surface of the outer shaft, and a distal end region, wherein the distal end region includes a distal-most tip defining a window in the outer shaft proximal along the axis to the distal-most tip;
an inner shaft coaxially maintained within the outer shaft such that the inner shaft is movable about the axis with respect to the outer shaft, wherein a portion of the inner shaft is exposed in the window of the outer shaft;
wherein the inner shaft includes an outer surface of the inner shaft and an inner surface of the inner shaft forming an axial lumen, wherein the inner surface of the inner shaft is exposed in the window while in an open configuration and the outer surface of the inner shaft is exposed in the window while in a closed configuration;
an exposed first electrode disposed on a first region of the outer surface of the outer shaft, the first region proximal along the axis to the window and on the distal end region and the first region having a first radius of the outer surface of the outer shaft;
an exposed fluid distribution outlet disposed on a second region of the outer surface of the outer shaft, the second region proximal along the axis to the exposed first electrode and the second region having a second radius of the outer surface of the outer shaft greater than the first radius; and
a second electrode electrically isolated from the exposed first electrode and disposed on the inner shaft, wherein the second electrode is exposed in the window of the outer shaft at least in one of the open configuration and the closed configuration;
wherein the outer surface of the inner shaft and an inner surface of the outer shaft define a lumen in fluid communication with the exposed fluid distribution outlet for delivering fluid to the exposed fluid distribution outlet via the lumen.

18. The electrosurgical device of claim 17 wherein the exposed fluid distribution outlet is configured to emit fluid across the exposed first electrode and toward the distal-most end.

19. The electrosurgical device of claim 18 further comprising a second fluid distribution outlet disposed on the outer surface of the outer shaft in a region distal along the axis to the exposed first electrode, wherein the exposed fluid distribution outlet is an exposed first fluid distribution outlet.

20. The electrosurgical device of claim 18 wherein the exposed first electrode is a sleeve having a circumferential portion distal to the exposed fluid distribution outlet.

21. The electrosurgical device of claim 17 wherein the exposed first electrode is directly mechanically coupled to the outer shaft.

22. The electrosurgical device of claim 17 wherein the elongate portion includes a conductive shaft covered with an electrically isolating material.

23. The electrosurgical device of claim 17 wherein the distal end region is configured from an insulator and the first electrode is disposed on the insulator.

* * * * *